(12) United States Patent
Goto et al.

(10) Patent No.: US 10,184,919 B2
(45) Date of Patent: Jan. 22, 2019

(54) FEEDBACK CONTROL APPARATUS

(71) Applicant: SHIMADZU CORPORATION, Kyoto-shi, Kyoto (JP)

(72) Inventors: Hiroomi Goto, Kyoto (JP); Tsunehiro Inoue, Kyoto (JP); Takahiro Mori, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/118,517

(22) PCT Filed: Dec. 11, 2014

(86) PCT No.: PCT/JP2014/082803
§ 371 (c)(1),
(2) Date: Oct. 24, 2016

(87) PCT Pub. No.: WO2015/122088
PCT Pub. Date: Aug. 20, 2015

(65) Prior Publication Data
US 2017/0045482 A1 Feb. 16, 2017

(30) Foreign Application Priority Data
Feb. 17, 2014 (JP) .................................. 2014-027870

(51) Int. Cl.
*G01N 30/32* (2006.01)
*G05D 16/20* (2006.01)
(Continued)

(52) U.S. Cl.
CPC ............. *G01N 30/32* (2013.01); *G05B 11/42* (2013.01); *G05B 19/46* (2013.01);
(Continued)

(58) Field of Classification Search
CPC .. G01N 30/00; G01N 30/32; G01N 2030/328; B01D 15/40; G05B 11/42;
(Continued)

(56) References Cited

U.S. PATENT DOCUMENTS 3,490,691 A * 1/1970 Takada .................. G05B 11/42
318/562
3,696,304 A * 10/1972 Fricke, Jr. .............. G05B 11/36
330/1 A
(Continued)

FOREIGN PATENT DOCUMENTS

GB 2125242 A * 2/1984 .............. H03M 1/48
JP 55-85906 A 6/1980
(Continued)

OTHER PUBLICATIONS

International Search Report of PCT/JP2014/082803, dated Jan. 20, 2015. [PCT/ISA/210].
(Continued)

*Primary Examiner* — Kenneth M Lo
*Assistant Examiner* — Mohammed Shafayet
(74) *Attorney, Agent, or Firm* — Sughrue Mion, PLLC

(57) ABSTRACT

A feedback control apparatus includes: a detector configured to detect an output value based on a controlled object; a P control circuit including a differential amplifier circuit and an analog circuit, the differential amplifier circuit being configured to receive a detection value of the detector and a target value, the analog circuit being configured to output a P control component $V_P$ to an output of the differential amplifier circuit; an I control unit configured to output an I control component $V_I$ by integrating a deviation of the detection value from the target value by digital processing; and a driver element configured to be driven based on the P control component $V_P$ from the P control circuit and the I
(Continued)

control component $V_I$ from the I control unit to control the controlled object.

9 Claims, 15 Drawing Sheets

(51) Int. Cl.
  *G05B 19/46* (2006.01)
  *G05B 11/42* (2006.01)
  *B01D 15/40* (2006.01)
(52) U.S. Cl.
  CPC ......... *G05D 16/2013* (2013.01); *B01D 15/40* (2013.01); *G01N 2030/328* (2013.01); *G05B 2219/41316* (2013.01); *G05B 2219/42034* (2013.01)
(58) Field of Classification Search
  CPC .................. G05B 6/02; G05B 19/46; G05B 2219/41316; G05B 2219/42034; G05D 16/2013
  USPC .............................................. 700/41; 318/609
  See application file for complete search history.

(56) References Cited

U.S. PATENT DOCUMENTS

| | | | | |
|---|---|---|---|---|
| 3,939,328 | A * | 2/1976 | Davis | F01D 17/24 290/40 R |
| 4,089,313 | A * | 5/1978 | Asano | F02D 41/1489 123/682 |
| 4,139,887 | A * | 2/1979 | Levesque, Jr. | G05B 11/32 318/609 |
| 4,228,435 | A * | 10/1980 | Nevin | G01S 13/89 342/173 |
| 4,658,855 | A * | 4/1987 | Doyle | G05D 7/0635 137/468 |
| 4,698,574 | A * | 10/1987 | Yoshizawa | G05B 11/42 110/190 |
| 4,733,152 | A * | 3/1988 | Allington | F04B 49/065 210/101 |
| 4,806,836 | A * | 2/1989 | Webb | G05B 5/01 318/609 |
| 5,059,880 | A * | 10/1991 | Hiroi | G05B 15/02 318/561 |
| 5,184,292 | A * | 2/1993 | Schneider | G05B 11/42 700/35 |
| 5,293,042 | A * | 3/1994 | Miyamoto | B82Y 35/00 250/307 |
| 5,493,488 | A * | 2/1996 | Castle | G05B 11/42 137/85 |
| 5,653,885 | A * | 8/1997 | Jameson | B01D 11/0203 210/149 |
| 5,764,017 | A * | 6/1998 | Bauck | G05B 11/42 318/610 |
| 6,445,980 | B1 * | 9/2002 | Vyers | G05B 11/42 318/609 |
| 7,395,124 | B2 * | 7/2008 | Schmidt | G05B 13/042 318/432 |
| 2002/0167431 | A1 * | 11/2002 | Poletto | G05B 11/42 341/126 |
| 2003/0094000 | A1 * | 5/2003 | Zagranski | F02C 9/28 60/773 |
| 2003/0101796 | A1 * | 6/2003 | Bolz | G01N 27/4065 73/23.31 |
| 2006/0001935 | A1 * | 1/2006 | Drake | G02B 6/266 359/13 |
| 2007/0157619 | A1 * | 7/2007 | Feiz | F02C 3/22 60/772 |
| 2007/0273709 | A1 * | 11/2007 | Kimura | G09G 5/397 345/619 |
| 2010/0122535 | A1 * | 5/2010 | Finkbeiner | F02C 7/22 60/734 |
| 2010/0140732 | A1 * | 6/2010 | Eminoglu | H01L 27/14634 257/447 |
| 2011/0233299 | A1 * | 9/2011 | Berger | G01N 30/28 239/76 |
| 2012/0082569 | A1 * | 4/2012 | Kanomata | G01L 9/0002 417/63 |
| 2012/0266623 | A1 * | 10/2012 | Patel | F25B 41/062 62/225 |

FOREIGN PATENT DOCUMENTS

| | | |
|---|---|---|
| JP | 62-148855 A | 7/1987 |
| JP | 3-207285 A | 9/1991 |
| JP | 6-309005 A | 11/1994 |
| JP | 3022050 B2 | 3/2000 |
| WO | 97/39521 A1 | 10/1997 |

OTHER PUBLICATIONS

Communication dated Sep. 11, 2017 issued by the European Patent Office in counterpart application No. 14882634.0.
Communication dated Sep. 28, 2017 issued by the European Patent Office in counterpart application No. 14882634.0.
K. R. Jahn et al: "Controlled Back Pressure Valve for Constant Flow and Pressure Programming in Packed Column Supercritical Fluid Chromatography", Analytical Chemistry, vol. 59, No. 2, 1 Jan. 1987, pp. 382-384, XP055401990 (3 pages total).
Communication dated Aug. 8, 2017, from Japanese Patent Office in counterpart application No. 2015-562702.
Communication dated Jul. 27, 2018 from the State Intellectual Property Office of the P.R.C. in counterpart Application No. 201480078024.7.

* cited by examiner

FEEDBACK CONTROL APPARATUS

CROSS REFERENCE TO RELATED APPLICATIONS

This application is a National Stage of International Application No. PCT/JP2014/082803 filed Dec. 11, 2014, claiming priority based on Japanese Patent Application No. 2014-027870, filed Feb. 17, 2014, the contents of all of which are incorporated herein by reference in their entirety.

TECHNICAL FIELD

The present invention relates to an apparatus that performs feedback control on a controlled object by a PI control scheme. Such a controlled object is widespread. Examples in an analyzer field include an apparatus that adjusts pressure and a flow rate in a flow channel such as a pressure-regulating valve, a pressure regulator, a back pressure regulator, a back pressure-regulating valve, and a flow controller. Examples in a field of manufacturing apparatus field include a semiconductor manufacturing apparatus and a positioning apparatus of a movable body in an industrial robot or NC machine. However, the controlled object to which the present invention is applied is not limited to these examples.

BACKGROUND ART

When a pressure control apparatus used in a super-critical fluid chromatograph (SFC) or super-critical fluid extractor (SFE) is cited as an example of controlled object, this apparatus performs feedback control on a degree of opening of the back pressure-regulating valve of the pressure control apparatus provided downstream of a detector of an analysis flow channel by using a piezoelectric element as a driver element, and controls pressure of a passing fluid (refer to Patent Documents 1, 2).

One feedback control method of a controlled object is a Proportional Integral (PI) control method. The PI control method performs feedback control on the controlled object by using a combination of a proportional component (P) and an integral component (I).

Methods for implementing the PI control method include an analog scheme using an electric circuit and a digital scheme that performs digital processing by software and the like (refer to Patent Documents 3, 4).

Among these schemes, the analog scheme may need a complicated, large-scale control circuit depending on the controlled object as will be described later, and control may become unstable. On the other hand, the digital scheme may not satisfy responsivity depending on the controlled object because A/D conversion, D/A conversion, and digital processing take time.

PRIOR ART DOCUMENTS

Patent Documents

Patent Document 1: Japanese Patent Laid-open Publication No. 03-172688

Patent Document 2: US Patent Application Publication No. 2010/0199982 A1

Patent Document 3: Japanese Patent No. 2844137

Patent Document 4: Japanese Patent No. 5382393

SUMMARY OF THE INVENTION

Problems to be Solved by the Invention

An object of the present invention is to provide a feedback control apparatus that facilitates implementation and satisfies responsivity.

Solutions to the Problems

The present invention performs P control by the analog scheme using an electric circuit, and performs I control by digital processing. That is, the present invention performs PI control of a combination of analog P control and digital I control.

Therefore, a feedback control apparatus according to the present invention includes: a detector configured to detect an output value based on a controlled object; a P control circuit including a differential amplifier circuit and an analog circuit, the differential amplifier circuit being configured to receive a detection value of the detector and a target value, the analog circuit being configured to output a P control component $V_P$ to an output of the differential amplifier circuit; an I control unit configured to output an I control component $V_I$ by integrating a deviation of the detection value from the target value by digital processing; and a driver element configured to be driven based on the P control component $V_P$ from the P control circuit and the I control component $V_I$ from the I control unit to control the controlled object.

Effects of the Invention

Stability of feedback control is high because P control can be performed by using an electric circuit independent of I control. Also, complicated processing can be implemented easily because I control is performed by digital processing.

In contrast, the scheme of Patent Document 3 or 4, which performs all PI control by digital processing, has a problem in responsivity depending on the controlled object. For example, for pressure control, the P control requires about 1-millisecond responsivity, and such high-speed processing is difficult from a viewpoint of analog-to-digital (A/D) and digital-to-analog (D/A) conversion time, and speed limit of software or firmware. Therefore, preferably the P control is performed by using an analog circuit. On the other hand, for I control, a response speed of about 10 milliseconds is sufficient because of an integral element, and it is suitable to perform I control by digital processing capable of performing complicated processing.

Therefore, the present invention is a scheme for effectively utilizing excellent characteristics of both the analog scheme and the digital scheme.

EMBODIMENTS OF THE INVENTION

Figure 1:
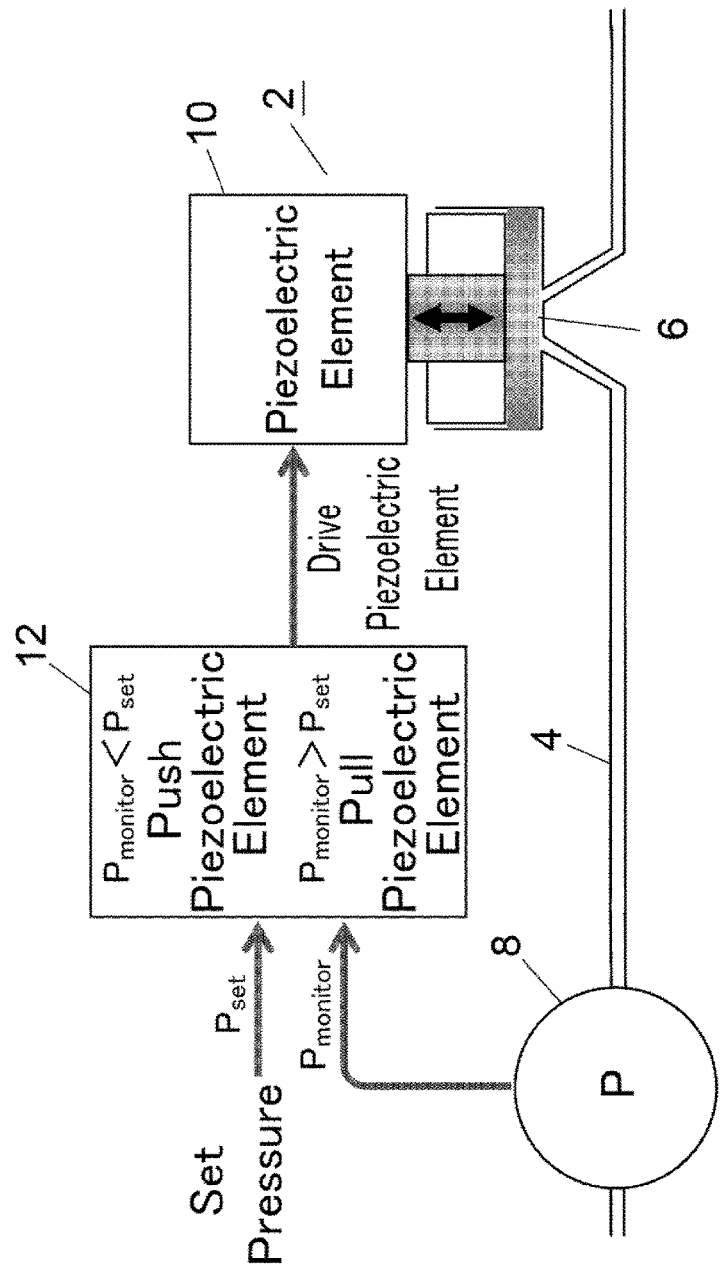
FIG. 1 is a schematic diagram illustrating a concept of pressure control performed by a back pressure regulator (BPR).

In the present invention, a preferred form for further simplifying a circuit configuration is a configuration in which an I control unit is connected to a P control circuit so that an I control component $V_I$ is input into one input terminal of the differential amplifier circuit together with a detection value of the detector, and an output terminal of the differential amplifier circuit is connected to the driver element.

In one preferred exemplary embodiment, the I control unit further includes a threshold holding unit that holds a threshold $V_{P\_upper}$ with respect to a deviation of the detection value from a target value, and a first comparison unit that resets the I control component $V_I$ of output to zero when the deviation exceeds the threshold $V_{P\_upper}$ held in the threshold holding unit, and continues integration of the deviation when the deviation is equal to or less than the threshold $V_{P\_upper}$ held in the threshold holding unit.

In another preferred exemplary embodiment, the I control unit further includes an upper limit holding unit that holds an upper limit $V_{I\_MAX}$ of an absolute value $|V_I|$ of the I control component $V_I$, and a second comparison unit that compares the I control component $V_I$ with the upper limit held in the upper limit holding unit and performs control so that the absolute value $|V_I|$ of an I control component $V_I$ output value does not exceed the upper limit.

An object to which a feedback control apparatus of the present invention is applied is not particularly limited, and a super-critical fluid chromatograph (SFC) or a super-critical fluid extractor (SFE) can be cited as one example. Here, the controlled object is a back pressure-regulating valve of a pressure control apparatus provided downstream of the detector of an analysis flow channel of the SFC or SFE. The detector is a pressure gauge provided upstream of the back pressure-regulating valve in the analysis flow channel, and the driver element is an actuator that controls the back pressure-regulating valve. In this case, the feedback control apparatus performs PI control on the back pressure-regulating valve based on the detection value of the pressure gauge and the target value.

The SFC will be described below as an example, but the example is not limited to the SFC.

The SFC uses a super-critical fluid as a mobile phase, and in order to prevent vaporization of the mobile phase, the SFC maintains the analysis flow channel in a constant high-pressure state. As the pressure control apparatus that performs pressure control, a back pressure regulator (BPR) is provided downstream of the detector of the analysis flow channel. The back pressure regulator adjusts the back pressure-regulating valve with a piezoelectric element or a solenoid as an actuator. The back pressure regulator performs feedback control on a voltage applied to the piezoelectric element or the solenoid so that pressure detected by the pressure gauge provided immediately before upstream side of the back pressure-regulating valve becomes equal to a set value as a target value. The following describes a case where the piezoelectric element is used as an actuator.

A concept of pressure control to be performed by the BPR will be described with reference to FIG. 1. A BPR 2 controls a degree of opening of a valve 6 (degree of opening of the valve, specifically an opening area) installed in a flow channel 4, and controls pressure of a passing fluid. A pressure signal value from a pressure gauge 8 installed in the flow channel upstream of the BPR 2 is defined as a monitor pressure $P_{monitor}$, and when the monitor pressure $P_{monitor}$ is lower than a set pressure $P_{set}$, which is a target value, a control apparatus 12 pushes the valve 6 with a piezoelectric element 10, which is an actuator, reduces a flow channel cross section, and enhances pressure. Conversely, when the monitor pressure $P_{monitor}$ is higher than the set pressure $P_{set}$, the control apparatus 12 decreases the pressure by pulling the piezoelectric element 10 and enlarging the flow channel cross section.

PI control is employed as a pressure control scheme to be performed by feedback control in the BPR. The PI control is a method commonly used for feedback control of pressure. Before description of the PI control, P control will be described, and subsequently the PI control will be described.

(P Control)

An operation amount that actually pushes and pulls the piezoelectric element 10 is a fixed multiple of a difference between the set pressure $P_{set}$ and the monitoring pressure $P_{monitor}$. When a voltage value obtained from the pressure gauge 8 is $V_{P\_mon}$, a voltage value corresponding to the set pressure $P_{set}$ is $V_{P\_set}$, and gain is $K_P$, then a voltage $V_{PZT}$ that is output to the piezoelectric element 10 is expressed by Equation (1).

$$V_{PZT} = K_P(V_{P\_set} - V_{P\_mon}) \qquad (1)$$

Here, it is assumed for convenience that the pressure value [MPa] and the voltage value [V] have an identical numerical value, and a case is considered where the monitoring pressure $P_{monitor}$=19.96 MPa ($V_{P\_mon}$=19.96 V) is obtained by feedback control of gain $K_P$=100 when the set pressure $P_{set}$=20.00 MPa ($V_{P\_set}$=20.00 V). At this time, an output voltage to the piezoelectric element becomes 100×(20.00−19.96)=4 V by Equation (1). However, when the degree of opening of the valve 6 by which position control is performed with an output of 4 V to the piezoelectric element 10 is the degree of opening that maintains the fluid at exactly 19.96 MPa, the BPR 2 will be in equilibrium by Equation (1), and the pressure will not converge on the target of 20 MPa. This residual 0.04 MPa is referred to as a steady-state deviation (offset), and the PI control is used to solve the steady-state deviation.

(PI Control)

The PI control is obtained by adding an integral term to Equation (1), and performs control expressed by Equation (2).

$$V_{PZT}=K_P(V_{P\_set}-V_{P\_mon})+K_I\int(V_{P\_set}-V_{P\_mon})dt \qquad (2)$$

Even if a left side $V_{PZT}$ is balanced with a first term of a right side, by an integral element of a second term of Equation (2), the second term of the right side is amplified until $V_{P\_set}$ and $V_{P\_mon}$ become an identical value. Accordingly, by continuously increasing or decreasing an amount of pushing the piezoelectric element 10, the pressure can be continuously increased or decreased until the pressure agrees with the target value.

Figure 2A:
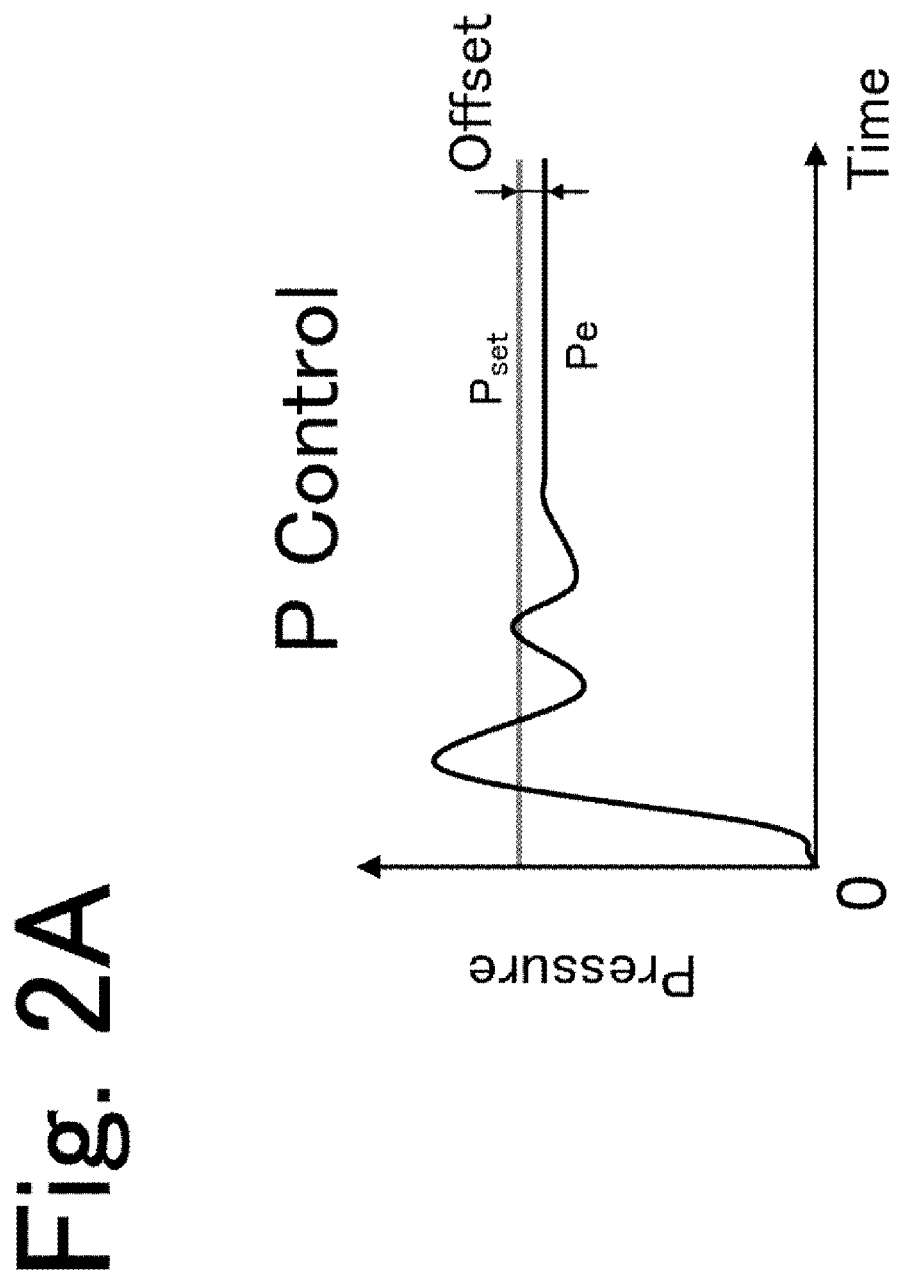
FIG. 2A is a graph illustrating a concept of a step response of P control.
Figure 2B:
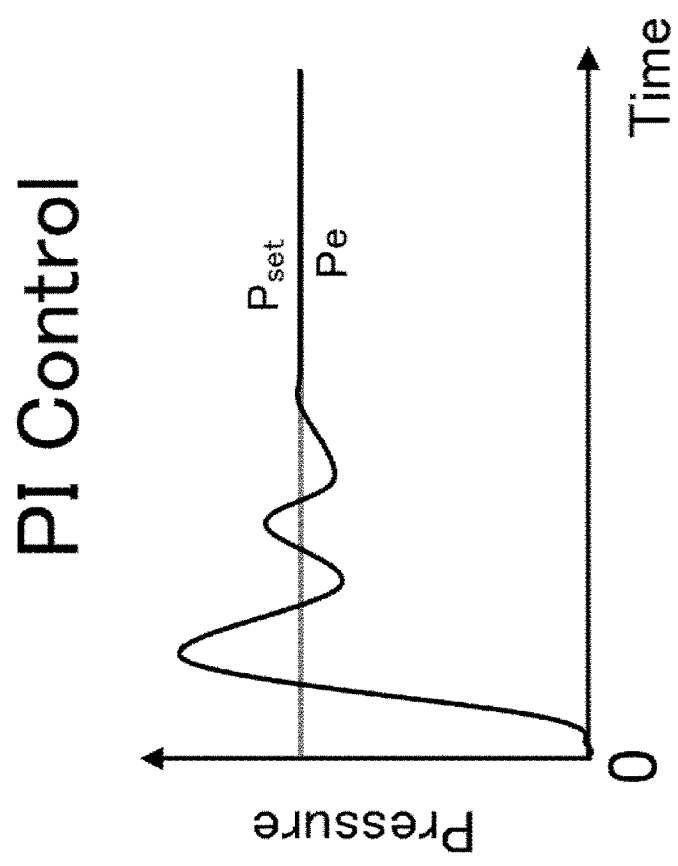
FIG. 2B is a graph illustrating the concept of the step response of PI control.

FIG. 2A and FIG. 2B illustrate conceptual diagrams of step response of the P control (FIG. 2A) and the PI control (FIG. 2B), respectively. When the certain target pressure value $P_{set}$ is provided at time t=0, a pressure value $P_e$ in equilibrium has a certain steady-state deviation (offset) with respect to $P_{set}$ in the P control, whereas $P_{set}$ agrees with $P_e$ in the PI control.

Figure 3:
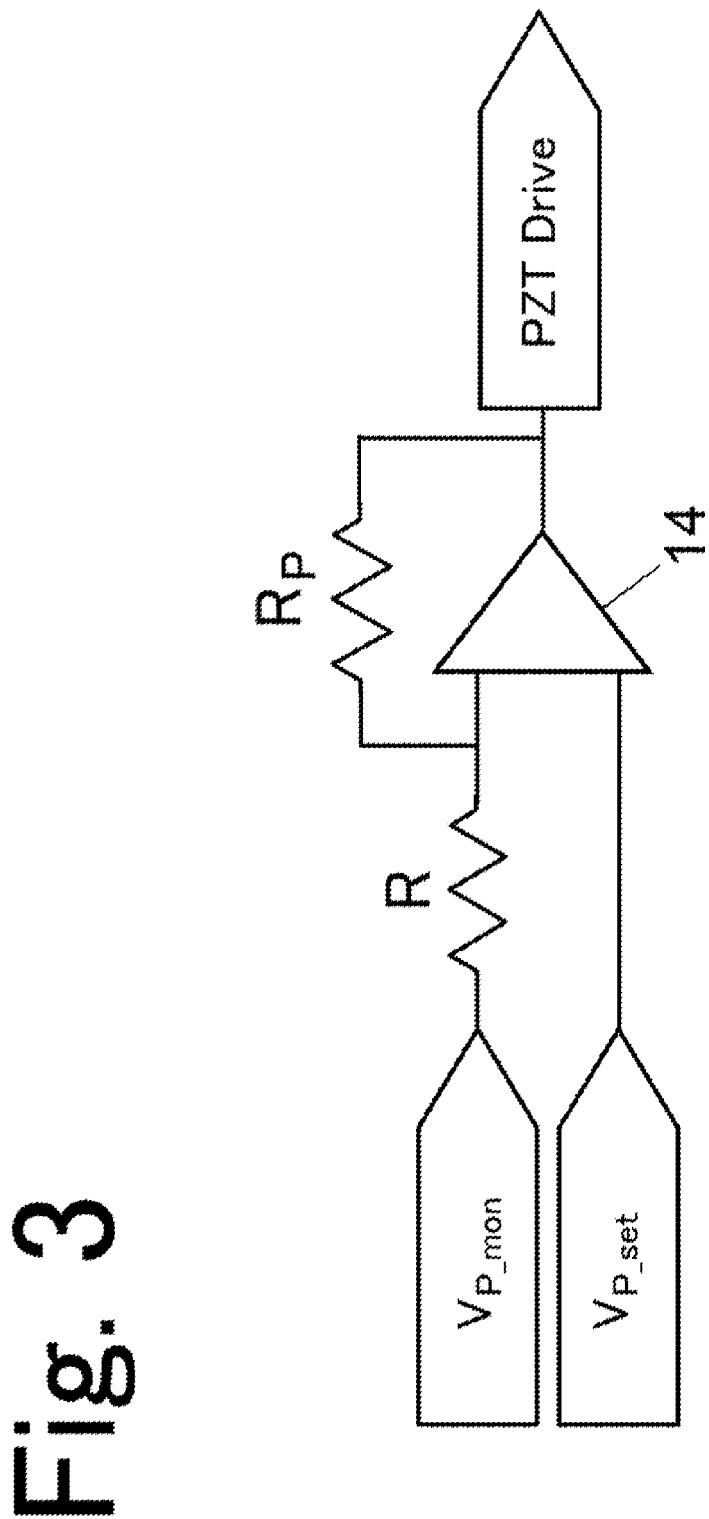
FIG. 3 is a circuit diagram illustrating one example of an electric circuit for performing P control.

FIG. 3 illustrates one example of an electric circuit for performing the P control. This electric circuit is a differential amplifier circuit that uses an operational amplifier circuit (operational amplifier) 14, amplifies a voltage difference between $V_{P\_mon}$ and $V_{P\_set}$ by a gain of a resistance ratio $R_P/R$ (corresponding to $K_P$ in Equation (1)), and outputs a voltage to the piezoelectric element 10 (illustrated as PZT Drive).

Figure 4:
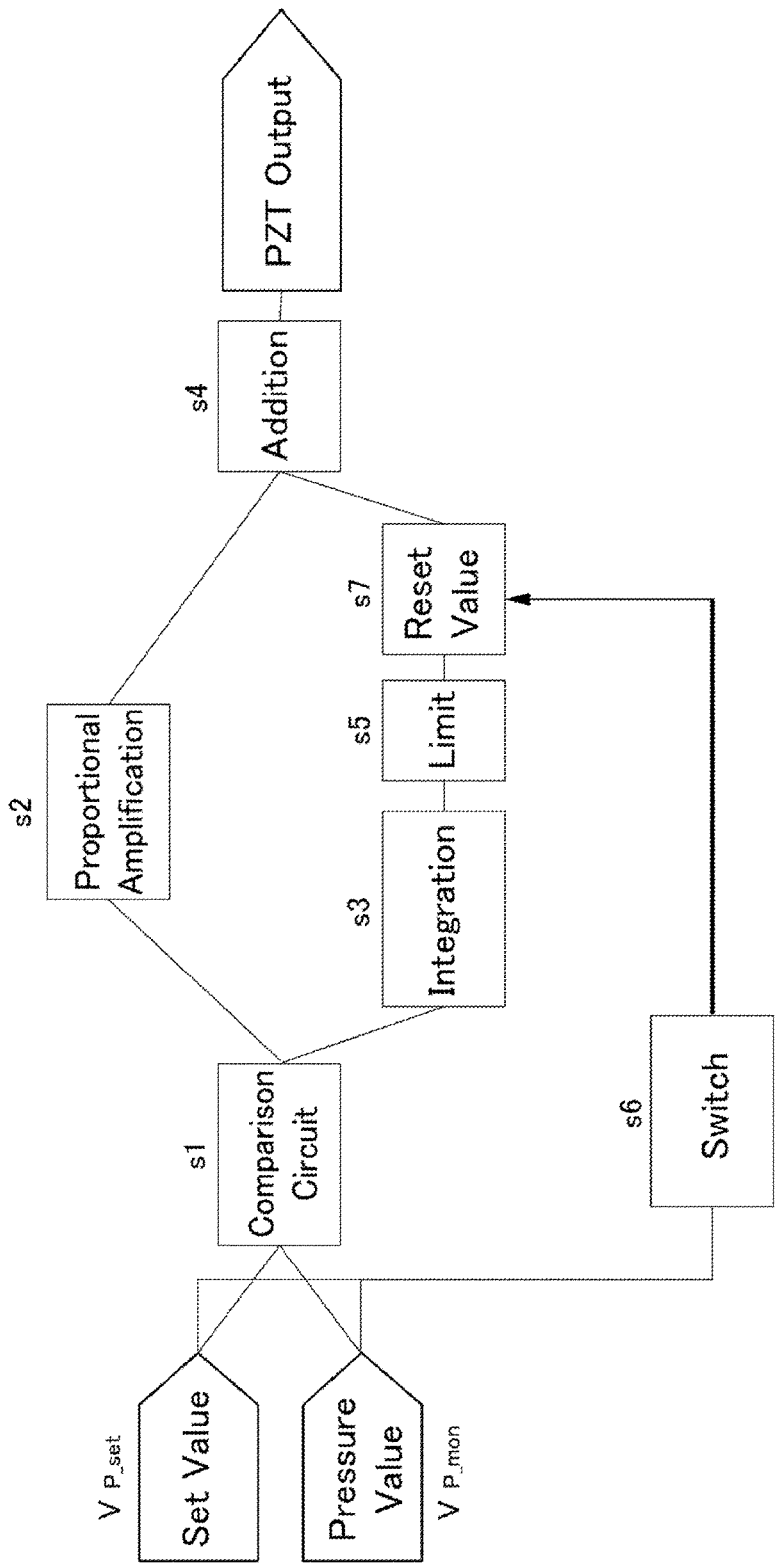
FIG. 4 is a block diagram illustrating an example of a control function necessary for PI control.

Although the PI control is performed because the steady-state deviation occurs in the P control, a PI control circuit needs a plurality of functions in an actual pressure control apparatus, leading to a complicated circuit. FIG. 4 illustrates an example of control functions necessary for the PI control. A comparison circuit for comparing a size of a set value $V_{P\_set}$ with a size of a monitor value $V_{P\_mon}$ (s1) is provided, and a proportional amplifier circuit which amplifies a comparison result for the P control (s2), an integrating circuit for the I control (s3), and a circuit for adding a P control component to the I control component (s4) are required first. Moreover, during pressure control in the SFC or SFE, a problem occurs that, when a pump is stopped or a flow channel is switched, even if a voltage is output to a maximum of an operation range of the piezoelectric element 10, the pressure does not become the set value but an excessive integrated value accumulates. For this reason, a circuit that limits the integrated value to an appropriate range (s5) is required. In addition, functions are also required to determine that the pressure value greatly deviates from the set value (s6), and to reset the integrated value to 0 in this case (s7). Implementation of the control illustrated in FIG. 4 as it is in an electric circuit leads to a large-scale, complicated control circuit, and may have adverse influence on the P control for performing stable control on the pressure.

Therefore, this exemplary embodiment performs so-called PI control of a mixture of analog P control and digital I control to perform the P control by using the electric circuit as illustrated in FIG. 3, and to perform the I control by digital processing (software (S/W), firmware (F/W), or a field-programmable gate array (FPGA)).

The FPGA is a type of digital circuit, and uses collective logic LSIs. The FPGA allows simple production of an electric circuit (integrated circuit) that performs a completely identical operation only by writing of software, and the FPGA has very high ease of implementation. When the FPGA is used in an analog signal system, an A/D converter is provided on an input side, and a D/A converter is provided on an output side. Even if the FPGA that performs the I control has a complicated circuit configuration, the FPGA is connected to an analog circuit for the P control via the D/A converter, and thus, stability of the P control is not affected.

Figure 5:
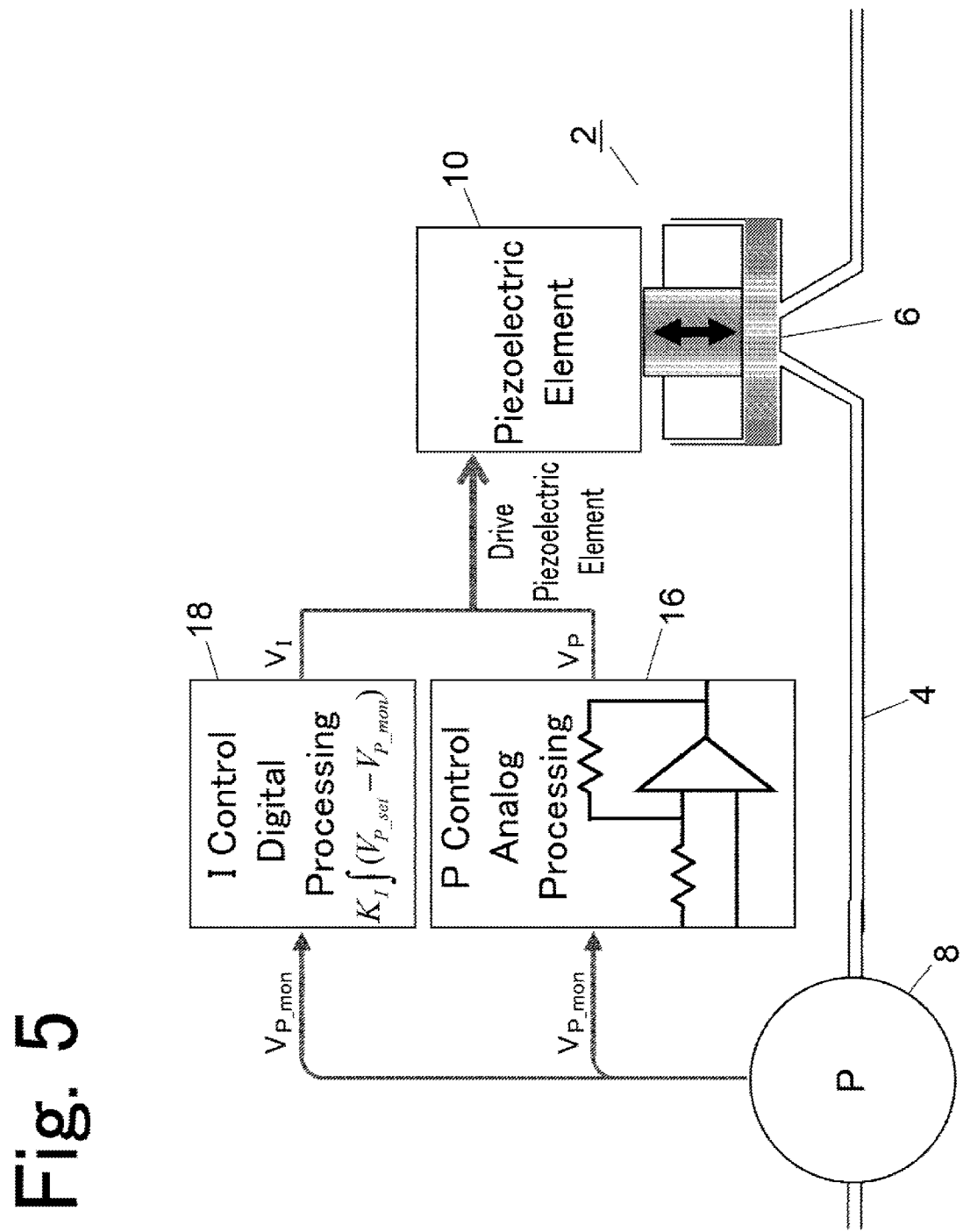
FIG. 5 is a block diagram schematically illustrating one exemplary embodiment.

FIG. 5 illustrates a conceptual diagram of control. The voltage value $V_{P\_mon}$ from the pressure gauge 8 is input into a P control circuit 16 including an analog circuit and an I control unit 18 that performs digital processing. The P control circuit 16 is, for example, the electric circuit illustrated in FIG. 3. The P control circuit 16 performs the P control on the voltage value $V_{P\_mon}$ and the set voltage value $V_{P\_set}$ corresponding to set pressure to output the P control component $V_P$. The I control unit 18 performs the I control on the voltage value $V_{P\_mon}$ and the set voltage value $V_{P\_set}$ by digital processing to output the I control component $V_I$. The P control component $V_P$ and the I control component $V_I$ are added to each other to drive the piezoelectric element 10, which is an actuator.

Figure 6:
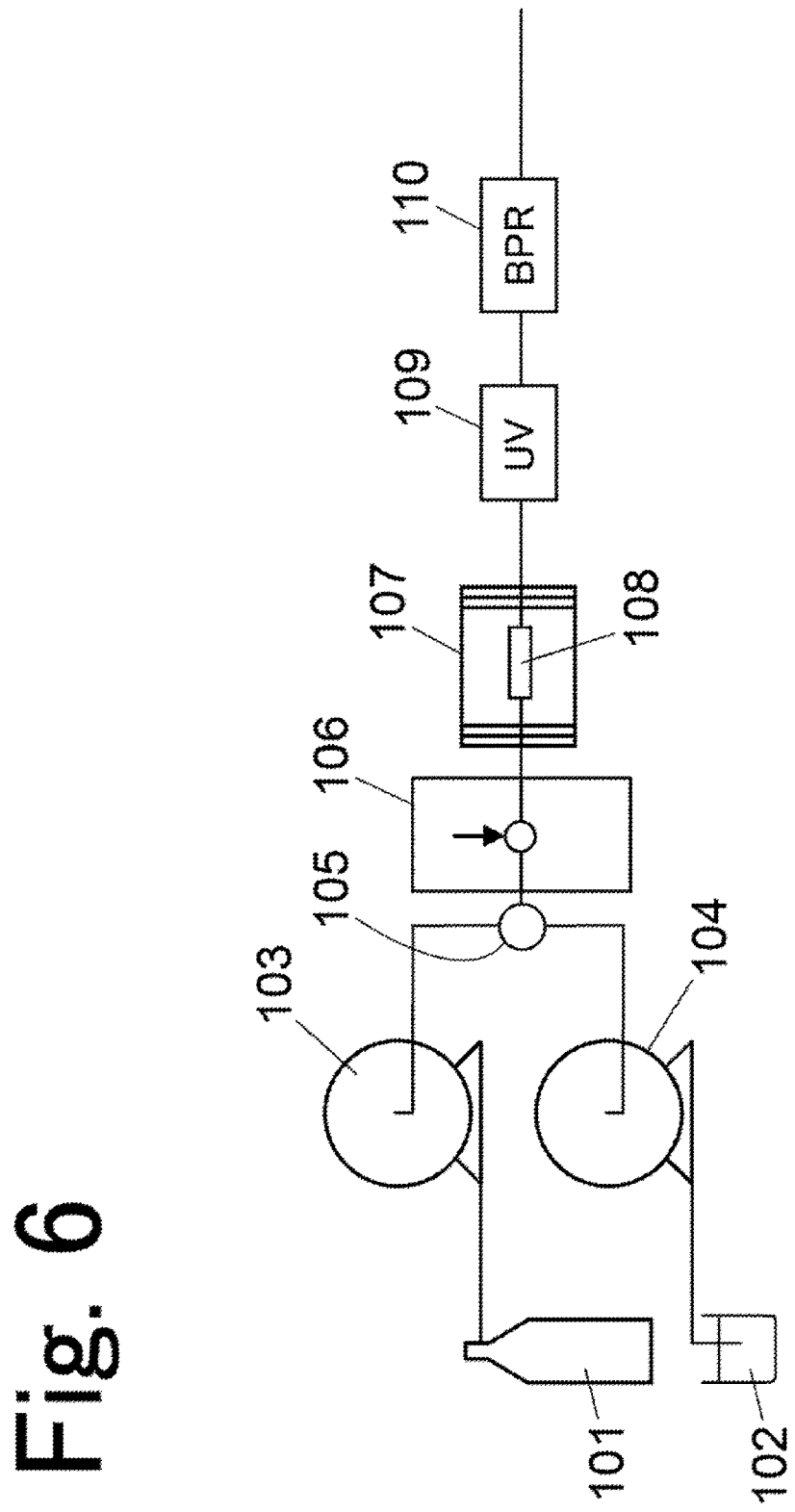
FIG. 6 is a schematic diagram illustrating an apparatus configuration of super-critical fluid chromatography (SFC).

Here, as an example to which the present invention is applied, an apparatus configuration of the super-critical fluid chromatograph (SFC) that uses the BPR will be described with reference to FIG. 6. The SFC uses $CO_2$ with which a super-critical state is obtained at relatively low temperature and low pressure as a mobile phase, and mixes a modifier (mainly methanol) to increase solubility of a measurement sample. For this purpose, a liquid $CO_2$ obtained from a $CO_2$ cylinder 101 is sent by a $CO_2$ pump 103, and a modifier 102 is similarly sent by a modifier pump 104. Then, a mixer 105 mixes the liquid $CO_2$ and the modifier 102 to make a mobile phase. The mobile phase into which a sample is injected by an automatic sampler 106 passes through a column 108 installed within a column oven 107, and a sample component is temporally separated in the column 108. The temporally separated sample component is detected by a UV detector 109.

A detection value of the UV detector 109 vastly changes depending on a density of a substance to be analyzed, and the super-critical fluid has large pressure dependence of density. Accordingly, the apparatus is configured so that pressure of the flow channel after the pumps 103, 104 is maintained at constant pressure equal to or greater than about 10 MPa by a pressure control valve 110 (back pressure regulator, BPR); however, pressure stability accuracy of a pressure-regulating valve greatly contributes to measurement stability of the UV detector 109. Accordingly, pressure control accuracy of about ±0.01 MPa is required with respect to the set pressure. In the SFC, in particular, a gradient analysis that temporally changes a mixing proportion of the modifier is commonly performed, and a great change in a composition of the fluid during the analysis causes fluctuating pressure.

Figure 7:
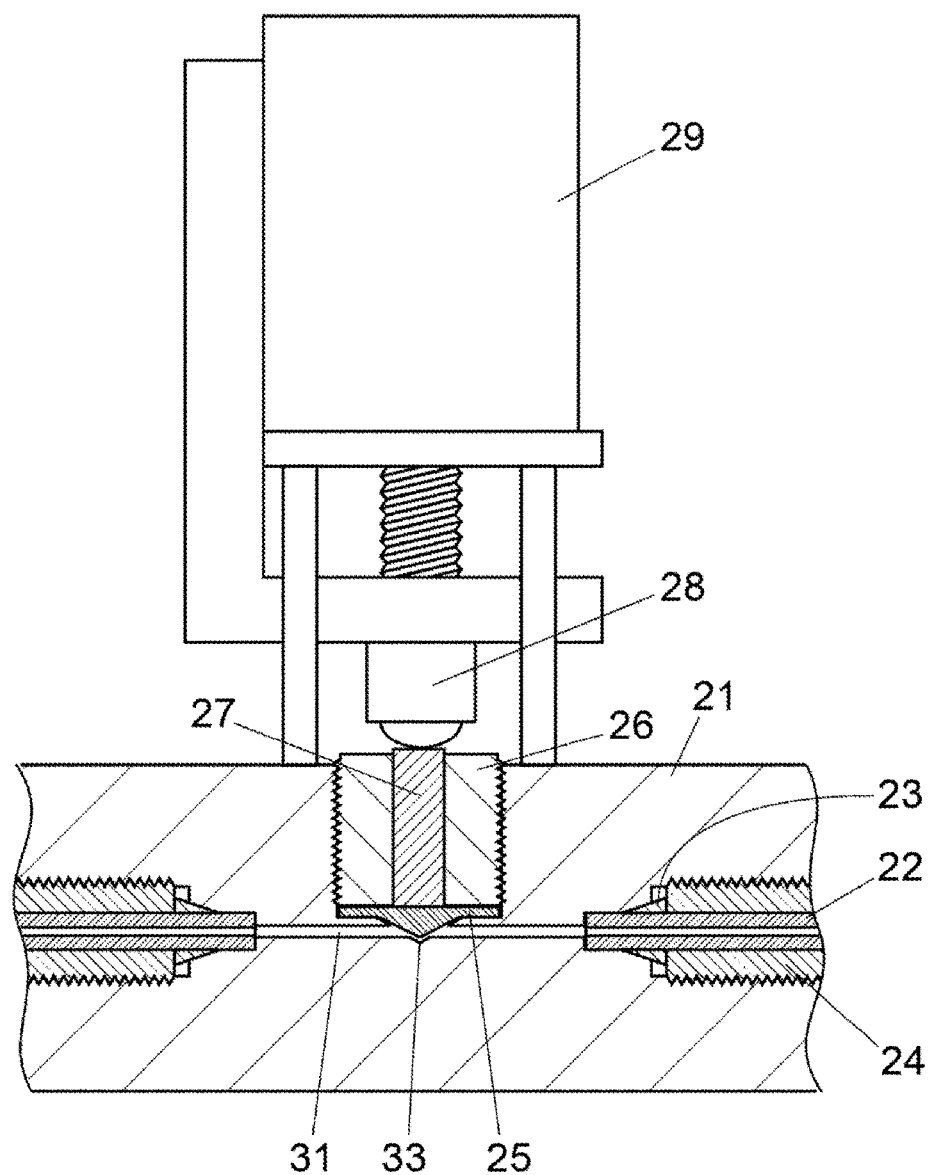
FIG. 7 is a cross-sectional view illustrating one example of a pressure-regulating valve used in an SFC system.

Next, one example of the pressure-regulating valve to be used in an SFC system will be described with reference to FIG. 7. Stainless steel pipes 22 with an inside diameter of 0.1 mm commonly used in the SFC are connected to an inlet and an outlet of a body 21. The body 21 is provided with a pipe flow channel 31 with an inside diameter of 0.3 mm, and both ends of the pipe flow channel 31 are connected to the stainless steel pipes 22. A center of each stainless steel pipe 22 is determined by a ferrule 23, and the stainless steel pipe 22 is fixed to the body 21 with a screw 24.

The body 21 is provided with a depression that disconnects the flow channel 31. A hole at the center of the depression is depressed in a shape of cone so as to disconnect the flow channel 31, and a cave connected to a section where the pipe flow channel 31 is disconnected is opened on a wall surface of the hole. The hole has a structure in which, when viewed from above, openings connected to an inlet side and outlet side of the flow channel come into sight on the wall surface of the conical depression. The hole is provided with a conical cover 25 made of an elastic body. The cover 25 has a structure in which a periphery of the cover is forced to a periphery of the hole by a seal member 26, and a section within the hole opens and closes the openings on the wall surface of the hole. The wall surface of the conical hole that disconnects the sealed minute flow channel 31 serves as a valve seat 33, whereas the cover 25 serves as a valve body.

Pushing and pulling a back surface of the cover 25 (opposite surface viewed from the hole) by a piezoelectric element 28 via a pressure bar 27 makes it possible to control an area of the flow channel of the valve seat 33, and to control pressure of the inlet pipe.

The piezoelectric element 28 is a piezoelectric actuator that is displaced about 10 μm when a voltage is applied from 0 V to 100V. In order to perform a coarse adjustment to displace the valve body in a wider range, a stepping motor 29 is attached to a subsequent stage of the piezoelectric element 28 viewed from the valve body.

Here, control of the piezoelectric actuator will be described. In the P control performed by the circuit diagram illustrated in FIG. 3, a deviation of about ±0.1 MPa (steady-state deviation) occurs between equilibrium pressure after the control and the set pressure. Moreover, a value of this steady-state deviation is dependent on an equilibrium potential of the piezoelectric element, and equilibrium pressure will change in response to a piezoelectric potential that is changed in response to a composition of the fluid that changes every moment during the gradient analysis. In order to avoid this, the PI control is preferably used as feedback control.

However, in the SFC and SFE to which the BPR is applied, complicated processing is required to the I control when the PI control is used. Examples of the complicated processing include: if a pump is stopped and a pressure value greatly deviates from the set value, the integrated value is reset to 0; if a time period is long during which pressure does not slightly reach the set value after the flow channel is switched, the excessive integrated value will accumulate, and thus, accumulation of the excessive integrated value is prevented; and momentary transitional pressure increase at the time of injecting a sample into the analysis flow channel is disregarded. Implementing such processing using an electric circuit will cause a problem that the circuit will become complicated and large-scale, which increases a noise and affects performance of the P control, and thus, ideal pressure stability is not obtained.

Figure 8:
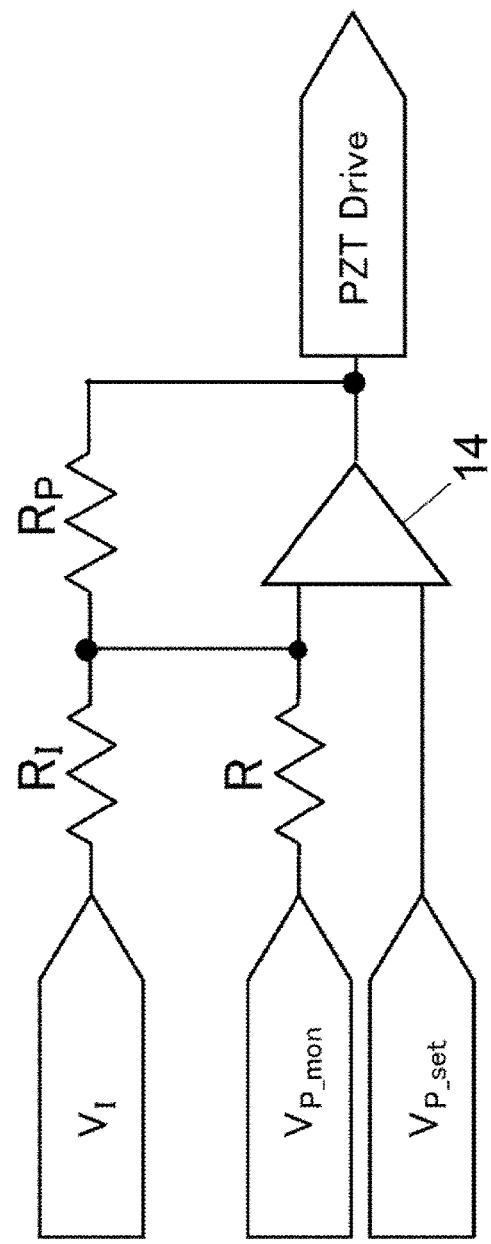
FIG. 8 is a circuit diagram illustrating one exemplary embodiment of PI control.

Therefore, in one preferred exemplary embodiment, the electric circuit illustrated in FIG. 8 performs the PI control. A differential amplifier circuit 14 using an operational amplifier performs feedback control so that the voltage value $V_{P\_mon}$ from the pressure gauge and the voltage value $V_{P\_set}$ corresponding to the set pressure may become identical to each other. An I control signal $V_I$ calculated by software or firmware is added to an input terminal to which the voltage value $V_{P\_mon}$ from the pressure gauge is input, among input terminals of the differential amplifier circuit 14.

Equation (3) expresses calculation to be performed by software or firmware for determining the I control signal $V_I$.

$$V_I = K_I \int (V_{P\_set} - V_{P\_Mon}) dt \quad (3)$$

Here, $K_T$ is an integration gain and is properly adjusted according to the control system. The gain of the I control as a whole is expressed by $K_I R_F / R_I$ including an amplification factor of the electric circuit illustrated in FIG. 8.

Figure 9:
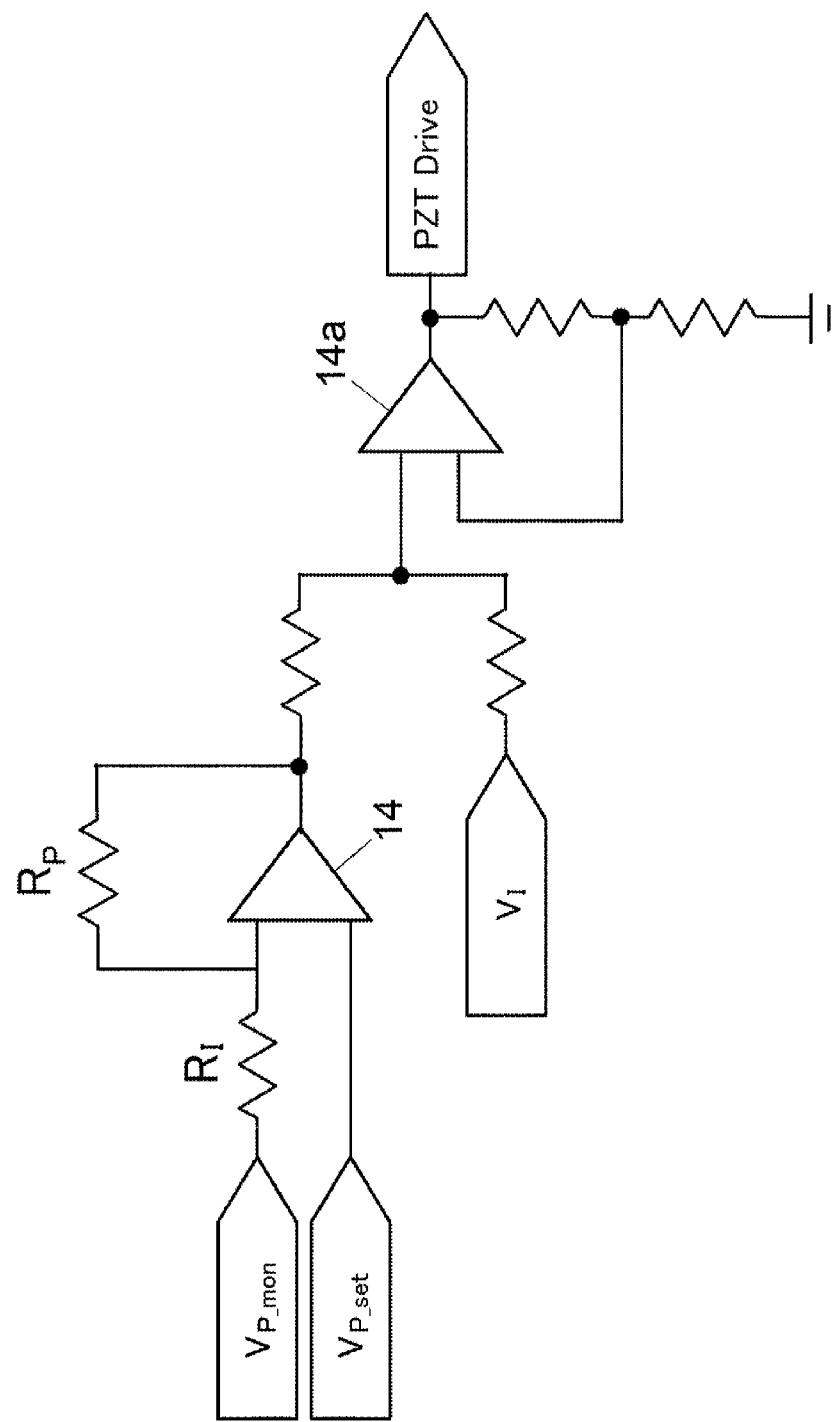
FIG. 9 is a circuit diagram illustrating another exemplary embodiment of PI control.

Addition of the I component $V_I$ to the P component $V_P$ is not limited to the circuit illustrated in FIG. 8, but can also be performed by a configuration as illustrated in FIG. 9 using a general adder circuit. However, the circuit of FIG. 9 requires an operational amplifier 14*a* for addition of the I component $V_I$ and the P component $V_P$ in addition to the operational amplifier 14 for the P control. Since one amplification stage increases, the circuit configuration of FIG. 8 with fewer amplification stages is more preferred from a viewpoint of stability. The circuit of FIG. 8 does not perform precise addition processing of a result of the P control and a result of the I control, and mathematically, the circuit of FIG. 8 does not perform the operation expressed by Equation (2). However, from a viewpoint that a piezoelectric voltage continues to increase or decrease until $V_{P\_set}$ and $V_{P\_mon}$ become identical to each other, the circuit of FIG. 8 performs identical processing, and eventually performs the PI control.

Figure 10:
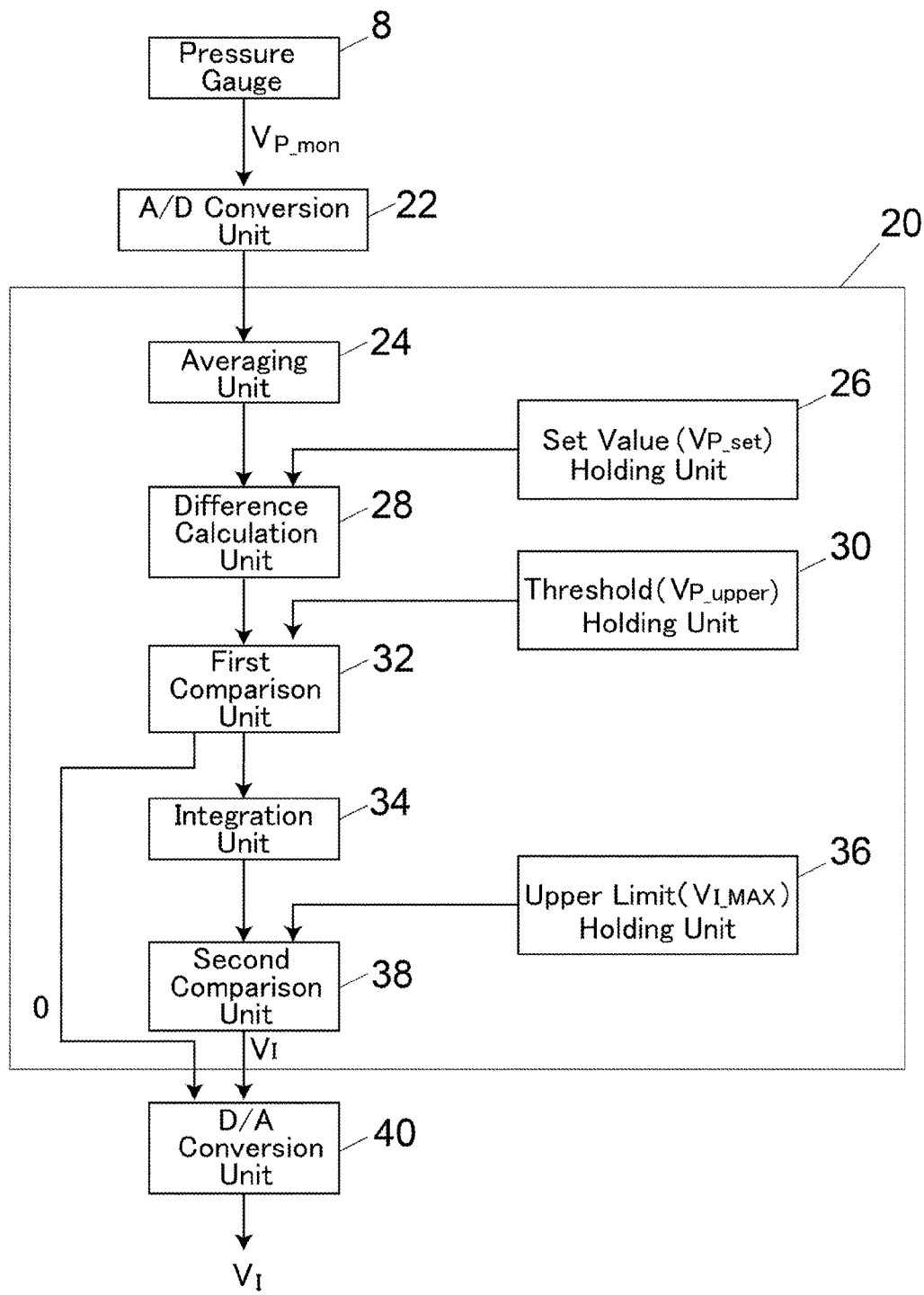
FIG. 10 is a block diagram illustrating one exemplary embodiment of an I control unit.
Figure 11:
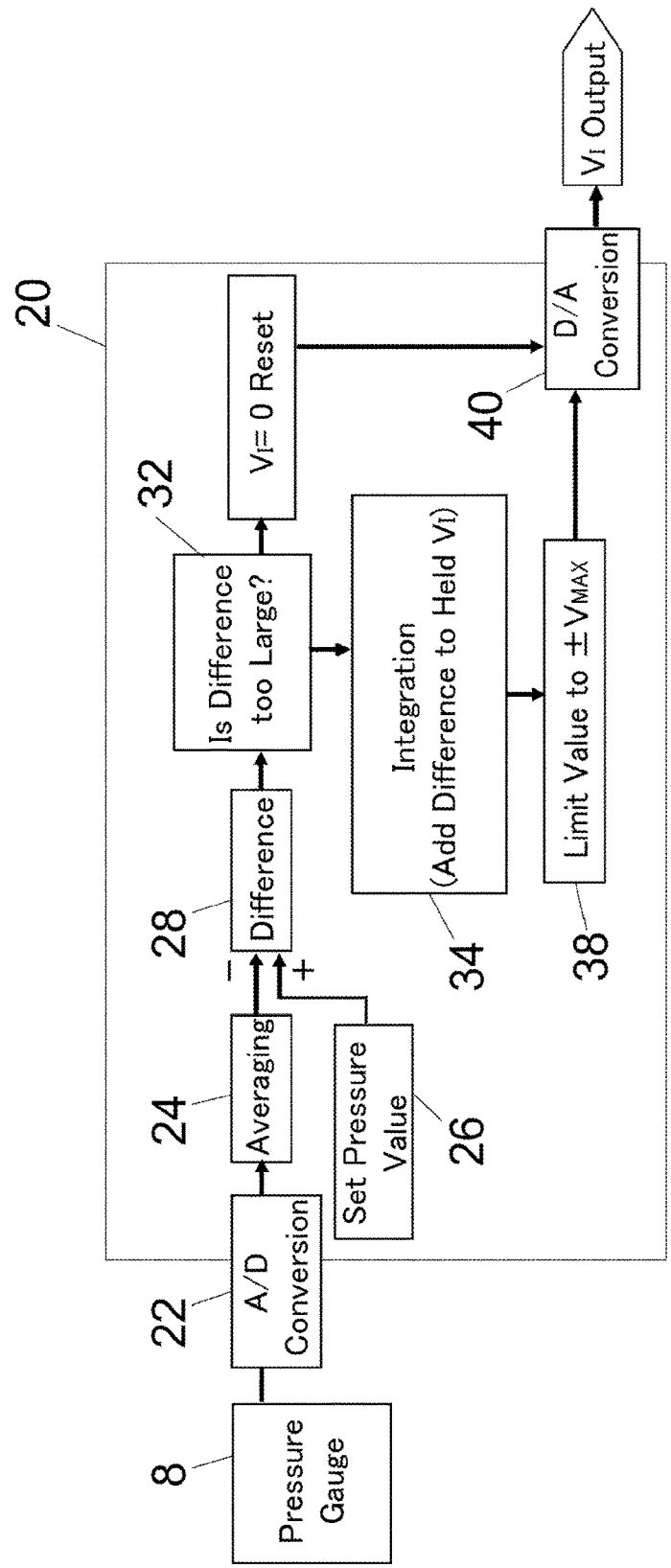
FIG. 11 is a block diagram illustrating a flow of processing of one exemplary embodiment of the I control unit.

FIG. 10 and FIG. 11 illustrate the digital processing as functions. A digital processing unit 20 is implemented by a computer dedicated to the SFC or SFE, or a general-purpose computer connected to the SFC or SFE for purposes such as data processing, for example, a personal computer.

In the digital processing, first, an A/D conversion unit 22 converts an analog voltage ($V_{P\_Mon}$) obtained from the pressure gauge 8 into a digital value. The A/D conversion unit 22 may be an A/D converter provided outside of the digital processing unit 20, and may be implemented as a function within the digital processing unit 20. Processing within the digital processing unit 20 is processed as a digital value.

An averaging unit 24 performs averaging processing on the obtained pressure value. The averaging processing is performed to eliminate a noise that occurs in the pressure gauge 8 and a noise that occurs during A/D conversion. The pressure value $V_{P\_Mon}$ after averaging is compared with the set pressure value $V_{P\_set}$, and a first comparison unit 28 calculates a difference therebetween. Both the pressure value $V_{P\_mon}$ and the set pressure value $V_{P\_set}$ are voltage values corresponding to pressure values. The set pressure value $V_{P\_set}$ can be generated by a circuit that generates a fixed voltage such as a reference voltage generating circuit, and the set pressure value $V_{P\_set}$ is provided from outside to the digital processing unit 20. The set pressure value $V_{P\_set}$ may be provided each time when the first comparison unit 28 calculates the difference, and as illustrated in FIG. 10, a set value holding unit 26 may be provided to hold the set pressure value $V_{P\_set}$.

When the calculation of the difference results in that the difference value is too large, the I control value $V_I$ accumulated so far is reset to zero. This is for the following reasons: The I control is originally intended to eliminate the steady-state deviation of the P control; when the P control is not performed and the pressure value is greatly deviated from the target, it is meaningless to perform integration; if the value of the I control value $V_I$ accumulates greatly when control enters a P control range, unnecessary time is needed until convergence on an appropriate I control value $V_I$, causing inconvenience. When the difference value is within an appropriate range, an integration unit 34 performs integration. The integration mentioned here is adding the difference value to the $V_I$ value that is currently held.

If the I control value $V_I$ after addition is within a reasonable range, a D/A conversion unit 40 converts the I control value $V_I$ as it is into an analog value to output the analog value to the electric circuit. If the I control value $V_I$ is outside the reasonable range, the I control value $V_I$ will be limited to the range and is output. In order to perform this limitation, an upper limit holding unit 36 holds an upper limit ($V_{I\_MAX}$), and a second comparison unit 38 compares the I control value $V_I$ after addition with the upper limit ($V_{I\_MAX}$) that is currently held in the upper limit holding unit 36.

A reason for this limitation is as follows. For example, when the flow channel is switched, $P\_{mon}$ has a value slightly lower than $P\_{set}$ (value that cannot be apparently distinguished from the steady-state deviation caused by the P control); however, it may take time for the fluid to fill the switched flow channel, and pressure may not increase easily. If the deviation is accumulated continuously during this period (if the I control value $V_I$ is continuously increased), when the flow channel is filled and the pressure increases, the pressure increases unnecessarily by the accumulated I control value $V_I$, reducing the I control value $V_I$ by calculation of Equation (3) takes time, and the pressure is not stabilized easily. Therefore, it is preferable to provide the upper limit for limitation.

Figure 12:
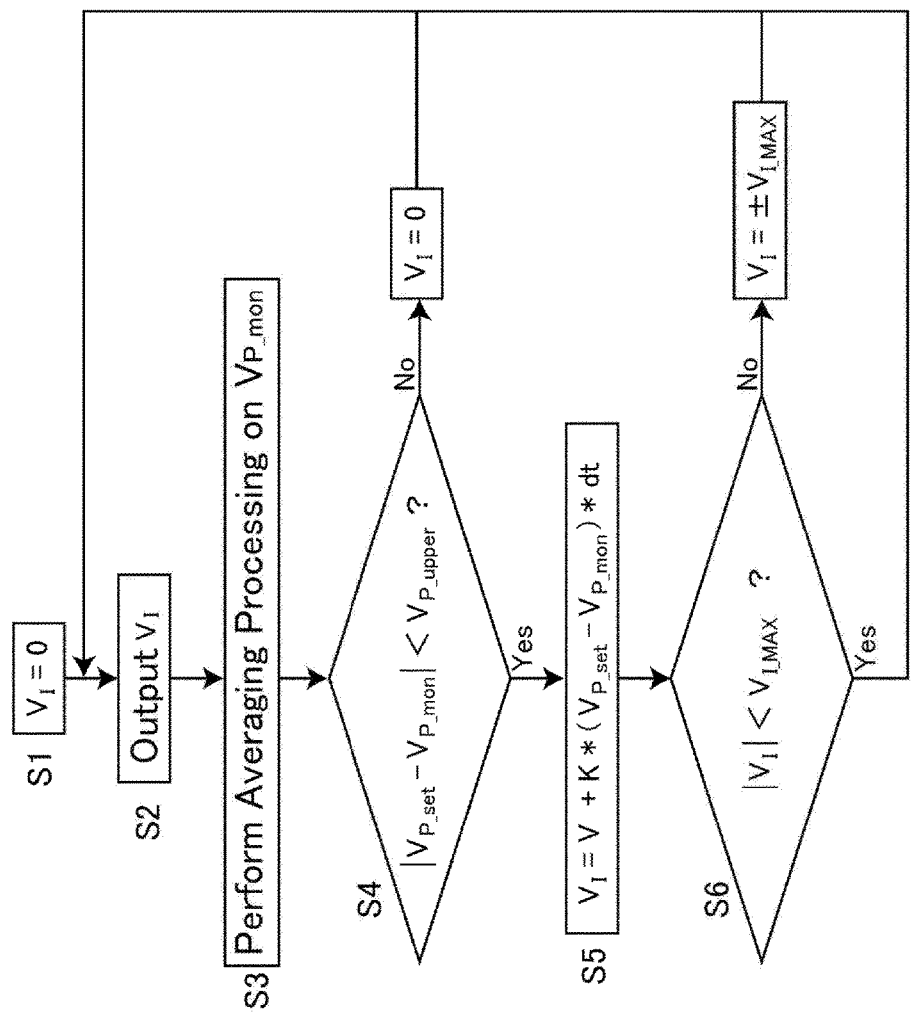
FIG. 12 is a flowchart illustrating a flow of processing of one exemplary embodiment of the I control unit.

FIG. 12 illustrates processing of FIG. 10 and FIG. 11 as a procedure in a flowchart. Before the control starts, an initial value of the I control value $V_I$ is 0 (step s1), and the I control value $V_I$ is output when the control starts (step s2). Next, the voltage value $V_{P\_mon}$ obtained from the pressure gauge 8 is averaged (step s3). When an absolute value of a difference between $V_{P\_mon}$ after averaging and the target set pressure value $V_{P\_set}$ exceeds a certain threshold $V_{P\_upper}$ (step s4), the I control value $V_I=0$, and the integrated value is reset. When the absolute value of the difference between $V_{P\_mon}$ after averaging and the set pressure value $V_{P\_set}$ is within $\pm V_{P\_upper}$, a value obtained by multiplication of $(V_{P\_set}-V_{P\_mon})$ by gain $K_I$ and processing time dt is added to the I control value $V_I$ that is held (step s5). Finally, in the case where an absolute value of the I control value $V_I$ of an integration result (after addition) exceeds a certain constant value $V_{I\_MAX}$, $V_I=V_{I\_MAX}$ when the I control value $V_I$ is a positive value, and $V_I=-V_{I\_MAX}$ when the I control value $V_I$ is a negative value. In the case where the absolute value of the I control value $V_I$ does not exceed $V_{I\_MAX}$ the value of the I control value $V_I$ is held as it is (step s6), and the processing returns to step s2 and changes an output value of the I control value $V_I$.

Figure 13A:
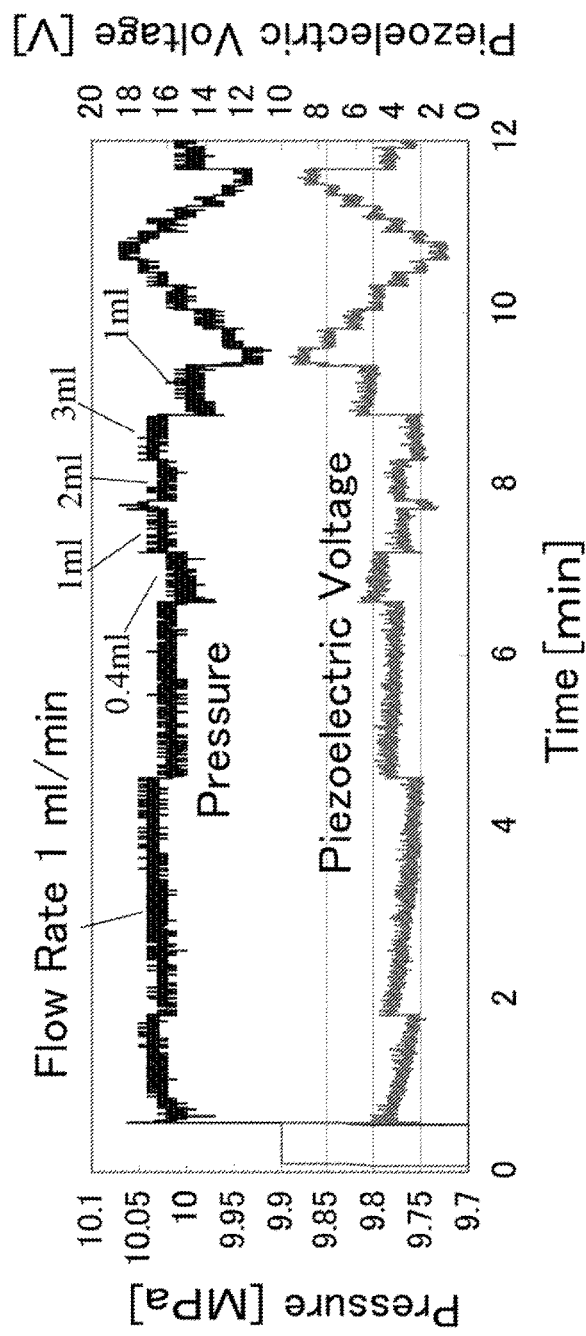
FIG. 13A is a graph illustrating a result of P control in one example.
Figure 13B:
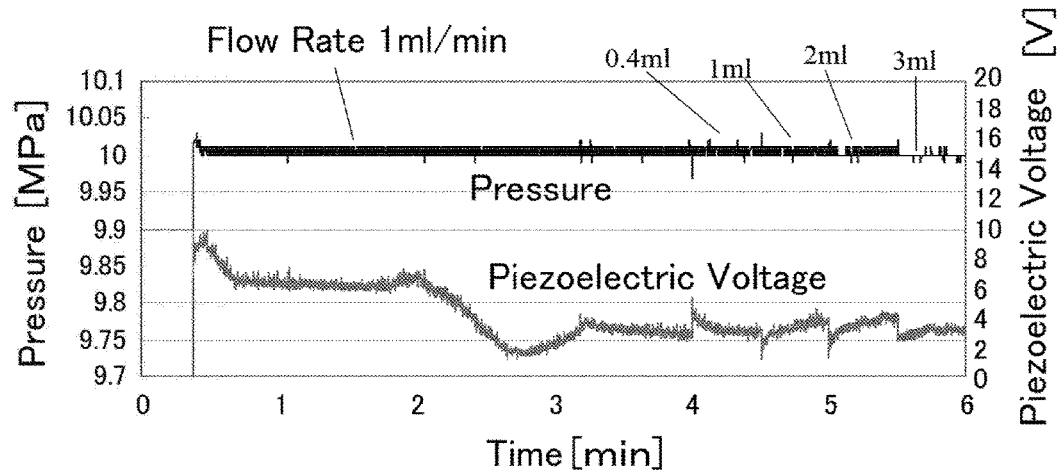
FIG. 13B is a graph illustrating a result of PI control in one example.

FIG. 13B illustrates an experimental result of performing pressure control in the examples of FIG. 8 and FIG. 10 to FIG. 12. FIG. 13A illustrates a case of performing only the P control for comparison. In either case of the P control and the PI control, the set value is 10.00 MPa, and the pressure value of the result of performing feedback control (upper graph in each diagram) and the piezoelectric voltage (lower graph in each diagram) are illustrated. Immediately after the pump starts to send the liquid, the condition is not stable, and the piezoelectric voltage changes to maintain constant pressure in both the P control and the PI control, resulting in a change in the value of the steady-state deviation and thus a slight change in the pressure.

In about six minutes, the pressure is balanced. In the case of only P control as illustrated FIG. 13A, the balanced pressure does not agree with 10.00 MPa, and an offset of about 0.02 MPa is generated. FIG. 13A demonstrates that, when the flow rate is changed thereafter, the pressure changes stepwise.

On the other hand, in the case of PI control of a mixture of analog P control and digital I control according to the present example, as illustrated in FIG. 13B, the pressure becomes stable immediately after the pump starts to send the liquid, and the pressure maintains the value of 10.00 MPa even if the flow rate is changed.

DESCRIPTION OF REFERENCE SIGNS

2: Back pressure regulator (BPR) as a controlled object
6: Valve
8: Pressure gauge as a detector
10: Piezoelectric element
14: Operational amplifier
16: P control circuit
18: I control unit
20: Digital processing unit
28: Difference calculation unit
30: Threshold holding unit
32: First comparison unit
34: Integration unit
36: Upper limit holding unit
38: Second comparison unit

The invention claimed is:

1. A feedback control apparatus comprising:
a detector configured to detect an output value based on a controlled object;
a P control circuit comprising a discrete differential amplifier circuit and a discrete analog circuit, the discrete differential amplifier circuit being configured to receive a detection value of the detector and a target value, the discrete analog circuit being configured to output a P control component $V_P$ to an output of the discrete differential amplifier circuit, the discrete differential amplifier circuit and the discrete analog circuit being separate circuits;
an I control section configured to output an I control component $V_I$ by integrating a deviation of the detection value from the target value by digital processing;
an analog adder circuit for adding the P control component $V_P$ from the P control circuit and the I control component $V_I$ from the I control section, the analog adder circuit is such that the output of the discrete differential amplifier circuit and the I control component $V_I$ are added to each other therein; and
a driver element configured to be driven based on the output of the analog adder circuit to control the controlled object.

2. The feedback control apparatus according to claim 1, wherein
the P control circuit is connected to the I control section so that the I control component $V_I$ is input into one input terminal of the discrete differential amplifier circuit together with the detection value of the detector, and
an output terminal of the discrete differential amplifier circuit is connected to the driver element.

3. The feedback control apparatus according to claim 1, wherein the I control section further comprises:
a threshold holding section configured to hold a threshold $V_{P\_upper}$ with respect to the deviation of the detection value from the target value; and
a first comparison section configured to reset the I control component $V_I$ of the output to zero when the deviation exceeds the threshold $V_{P\_upper}$ held in the threshold holding unit, and to continue integration of the deviation when the deviation is equal to or less than the threshold $V_{P\_upper}$ held in the threshold holding unit.

4. The feedback control apparatus according to claim 1, wherein the I control section further comprises:

an upper limit holding section configured to hold an upper limit $V_{I\_MAX}$ of the I control component $V_I$; and a second comparison section configured to compare the I control component $V_I$ with the upper limit held in the upper limit holding unit to perform control so that an I control component $V_I$ output value does not exceed the upper limit.

5. The feedback control apparatus according to claim 1, wherein the controlled object is a back pressure-regulating valve of a pressure control apparatus provided downstream of a detector of an analysis flow channel of one of a super-critical fluid chromatograph and a super-critical fluid extractor, the detector is a pressure gauge provided upstream of the back pressure-regulating valve in the analysis flow channel, the driver element is an actuator configured to control the back pressure-regulating valve, and PI control is performed on the back pressure-regulating valve based on a detection value of the pressure gauge and a target value.

6. The feedback control apparatus according to claim 2, wherein the controlled object is a back pressure-regulating valve of a pressure control apparatus provided downstream of a detector of an analysis flow channel of one of a super-critical fluid chromatograph and a super-critical fluid extractor, the detector is a pressure gauge provided upstream of the back pressure-regulating valve in the analysis flow channel, the driver element is an actuator configured to control the back pressure-regulating valve, and PI control is performed on the back pressure-regulating valve based on a detection value of the pressure gauge and a target value.

7. The feedback control apparatus according to claim 3, wherein the controlled object is a back pressure-regulating valve of a pressure control apparatus provided downstream of a detector of an analysis flow channel of one of a super-critical fluid chromatograph and a super-critical fluid extractor, the detector is a pressure gauge provided upstream of the back pressure-regulating valve in the analysis flow channel, the driver element is an actuator configured to control the back pressure-regulating valve, and PI control is performed on the back pressure-regulating valve based on a detection value of the pressure gauge and a target value.

8. The feedback control apparatus according to claim 4, wherein the controlled object is a back pressure-regulating valve of a pressure control apparatus provided downstream of a detector of an analysis flow channel of one of a super-critical fluid chromatograph and a super-critical fluid extractor, the detector is a pressure gauge provided upstream of the back pressure-regulating valve in the analysis flow channel, the driver element is an actuator configured to control the back pressure-regulating valve, and PI control is performed on the back pressure-regulating valve based on a detection value of the pressure gauge and a target value.

9. The feedback control apparatus according to claim 1, wherein the discrete analog circuit includes a resistor provided in parallel to a detection value input of the discrete differential amplifier circuit and the output of the discrete differential amplifier circuit.

* * * * *